US010772272B2

(12) United States Patent
Hazlebeck

(10) Patent No.: US 10,772,272 B2
(45) Date of Patent: Sep. 15, 2020

(54) ALGAE CULTIVATION SYSTEMS AND METHODS WITH REDUCED ENERGY LOSS

(71) Applicant: Global Algae Innovations, Inc., San Diego, CA (US)

(72) Inventor: David A. Hazlebeck, El Cajon, CA (US)

(73) Assignee: Global Algae Technologies, LLC, Santee, CA (US)

( * ) Notice: Subject to any disclaimer, the term of this patent is extended or adjusted under 35 U.S.C. 154(b) by 183 days.

(21) Appl. No.: 15/590,441

(22) Filed: May 9, 2017

(65) Prior Publication Data

US 2017/0318764 A1  Nov. 9, 2017

Related U.S. Application Data

(60) Provisional application No. 62/333,717, filed on May 9, 2016.

(51) Int. Cl.
| | |
|---|---|
| *A01G 33/00* | (2006.01) |
| *C12N 1/12* | (2006.01) |
| *C12M 1/00* | (2006.01) |
| *A01H 4/00* | (2006.01) |
| *A01H 13/00* | (2006.01) |

(52) U.S. Cl.
CPC ............. *A01G 33/00* (2013.01); *C12M 21/02* (2013.01); *C12M 23/18* (2013.01); *C12M 23/38* (2013.01); *C12M 31/08* (2013.01); *C12N 1/12* (2013.01); *A01H 4/00* (2013.01); *A01H 13/00* (2013.01); *Y02A 40/88* (2018.01)

(58) Field of Classification Search
CPC ....... A01G 33/00; C12M 21/02; C12M 23/18; C12M 23/38; C12M 31/08; A01H 4/001; C12N 1/12

USPC ............................................................. 47/1.4
See application file for complete search history.

(56) References Cited

U.S. PATENT DOCUMENTS

| | | |
|---|---|---|
| 2,732,662 A | 1/1956 | Myers et al. |
| 3,243,918 A | 4/1966 | Machiedo et al. |
| 4,253,271 A | 3/1981 | Raymond |
| 4,320,594 A | 3/1982 | Raymond |
| 5,981,271 A | 11/1999 | Doucha et al. |
| 8,245,440 B2 | 8/2012 | Ryan et al. |

(Continued)

FOREIGN PATENT DOCUMENTS

| | | | | |
|---|---|---|---|---|
| EP | 2875724 A1 | * | 5/2015 | ............. A01G 33/00 |
| GB | 2501101 A | * | 10/2013 | ............. A01G 33/00 |
| WO | 2013186626 | | 12/2013 | |

OTHER PUBLICATIONS

Liffman, K. et al., Comparing the energy efficiency of different high rate algal raceway pond designs using computational fluid dynamics. Chemical Engineering Research and Design, 2013, vol. 91 (2), 221-226.*

(Continued)

*Primary Examiner* — Kathleen I Alker
(74) *Attorney, Agent, or Firm* — Quarles & Brady LLP

(57) ABSTRACT

An open raceway algae cultivation system includes a channel configured to contain an algae cultivation fluid. The channel includes a contraction zone having a width and a depth. A pump is configured to circulate the algae cultivation fluid in the channel. A width of the contraction zone decreases leading into the entrance of the pump and a depth of the contraction zone is greater than a depth of at least a portion of the channel located outside of the contraction zone.

16 Claims, 4 Drawing Sheets

(56) References Cited

U.S. PATENT DOCUMENTS

| | | |
|---|---|---|
| 8,318,478 B2 | 11/2012 | Dahle |
| 8,541,225 B2 | 9/2013 | Hazlebeck et al. |
| 8,748,162 B2 | 6/2014 | Hazlebeck et al. |
| 8,752,329 B2 | 6/2014 | Parsheh et al. |
| 8,769,867 B2 | 7/2014 | Parsheh et al. |
| 2011/0217692 A1 | 9/2011 | Morgan et al. |
| 2011/0229775 A1 | 9/2011 | Michaels et al. |
| 2011/0287531 A1 | 11/2011 | Hazlebeck |
| 2012/0220027 A1 | 8/2012 | Miller, III et al. |
| 2012/0272574 A1* | 11/2012 | Parsheh ............... A01G 33/00 47/62 R |
| 2013/0269244 A1* | 10/2013 | Jovine .................. A01G 33/00 47/1.4 |
| 2015/0182923 A1 | 7/2015 | Malkiel et al. |
| 2017/0318771 A1* | 11/2017 | Hazlebeck ............ A01G 33/00 |

OTHER PUBLICATIONS

Yadala et al., A dynamic optimization model for designing open-channel raceway ponds for batch production of algal biomass. Processes, 2016, 4, 10.*
Dodd, "Elements of Pond Design and Construction," CRC Handbook of Microalgal Mass Culture, CRC Press 1986, pp. 265-283.
Chiaramonti et al., "Review of Energy Balance in Raceway Ponds for Microalgae Cultivation: Re-Thinking a Traditional System is Possible," Applied Energy 102, 2013, pp. 101-111.
International Search Report and Written Opinion for related International Patent Application No. PCT/US2017/031689, dated Aug. 16, 2017.

* cited by examiner

ALGAE CULTIVATION SYSTEMS AND METHODS WITH REDUCED ENERGY LOSS

CROSS-REFERENCE TO RELATED APPLICATION(S)

This application claims priority to U.S. provisional application No. 62/333,717, filed on May 9, 2016, which is incorporated by reference herein and relied upon in its entirety.

STATEMENT OF FEDERALLY SPONSORED RESEARCH OR DEVELOPMENT

This invention was made with government support under award # DE-EE0006314 and award # DE-EE0007689, both awarded by the Department of Energy ("DOE"), and under sub-recipient #06-S140633 of prime award # W911NF-14-2-0017 awarded by the Defense Advanced Research Projects Agency ("DARPA"). The government has certain rights in the invention.

BACKGROUND OF THE DISCLOSURE

The present disclosure relates generally to algae cultivation systems and methods, and more particularly to open raceway algae cultivation systems and methods.

Algae cultivation has become widely recognized as a promising source of food, biofuel, chemicals, and nutraceuticals. Open algae cultivation systems have been developed for large-scale cultivation. The energy to operate a pump that circulates algae cultivation fluid or slurry is an important operating cost in these open systems. Larger open systems typically have a zone in a channel width entering the pump, and zone in a channel width exiting the pump. The bottom of the channels in these systems are typically level or gently sloped, so the speed of the algae slurry is much higher in the zones entering and exiting the pumps than the velocity in the rest of the channel. The acceleration and the high velocity both result in large energy losses. For level raceways, the energy losses are even greater than sloped systems.

New and improved algae cultivation systems and methods are accordingly needed.

SUMMARY OF THE DISCLOSURE

In one aspect of the present disclosure, an open raceway algae cultivation system includes a channel configured to contain an algae cultivation fluid. The channel include a contraction zone having a width and a depth. A pump is configured to circulate the algae cultivation fluid in the channel and has an entrance and an exit. The width of the contraction zone decreases leading into the entrance of the pump, and the depth of the contraction zone is greater than a depth of at least a portion of the channel located outside of the contraction zone.

In another aspect, an open raceway algae cultivation system includes a channel configured to contain an algae cultivation fluid. The channel including an expansion zone having a width and a depth. A pump is configured to circulate the algae cultivation fluid in the channel and includes an entrance and an exit. The width of the expansion zone increases going away from the exit of the pump and the depth of the expansion zone is greater than a depth of at least a portion of the channel located outside of the expansion zone.

It should therefore be appreciated that is an objective of the present disclosure to reduce energy losses during the flow of algae cultivation fluid through an open raceway algae cultivation system.

DETAILED DESCRIPTION

Figure 1:
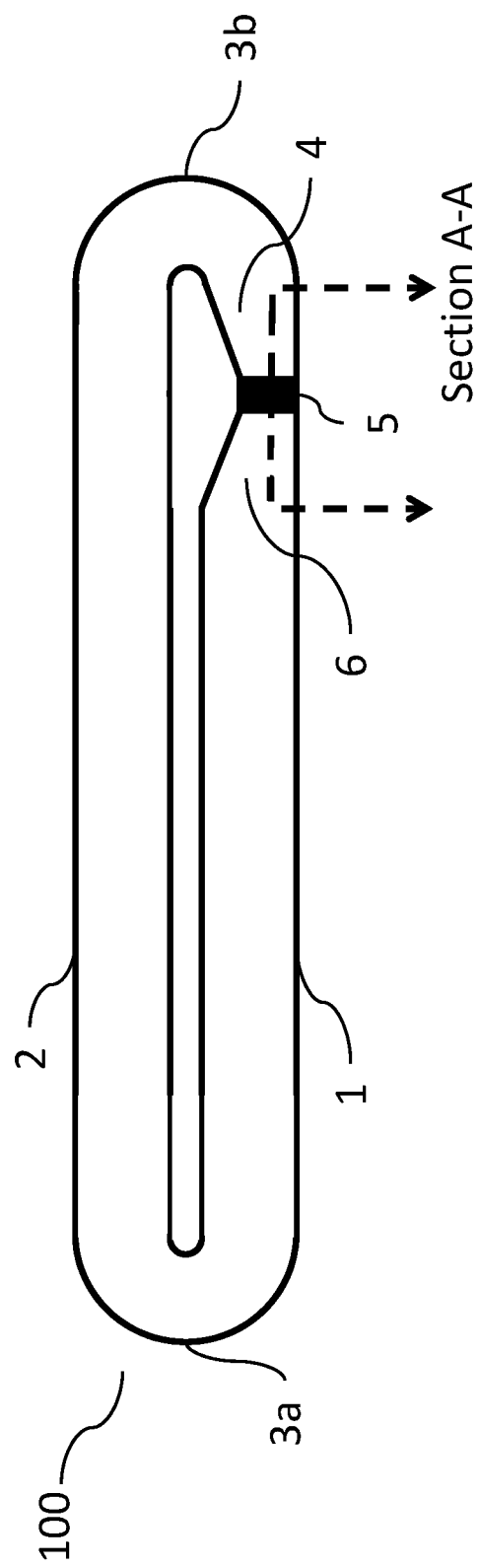
FIG. 1 is a plan view illustrating an open raceway algae cultivation system according to one embodiment of the present disclosure.

Referring now to the figures, FIG. 1 illustrates one non-limiting embodiment of an open raceway algae cultivation system of the present disclosure. The system includes a channel 100 having two conduits 1 and 2 fluidly coupled or connected to each other by bends 3a, 3b. An algae cultivation fluid or slurry is contained with the channel and circulated by a pump 5, which can be a paddlewheel, a propeller pump, an Archimedes screw pump, a fluid jet, or any other suitable structure or device for circulating or pumping the algae cultivation fluid through the channel 100. A width of pump 5 is less than a width of the conduits 1 and 2 so that leading into an entrance of the pump 5 there is a contraction zone 4 having a width that is less than a width of the channel 100 outside of the contraction zone 4. The reduced width of contraction zone 4 decreases from the portion outside the contraction zone 4 leading into the entrance of the pump 5. The width of pump 5 is also less than the conduits 1 and 2 so that going away from the exit of the pump 5, there is an expansion zone 6 having a width greater than the width of channel 100 outside the expansion zone 6. The increased width of expansion zone 6 increases going away from the exit of pump 5. When algae cultivation fluid is circulated in the channel 100 via pump 5, the fluid exits the pump 5, flows through the expansion zone 6, through the conduit 1, around bend 3a, through conduit 2, around bend 3b, through contraction zone 4, and back into the entrance of pump 5. The bottom of the conduits 1 and 2, as well as the bends 3a and 3b, can be level or sloped downwardly from the expansion zone 6 to the contraction zone 4.

Figure 2:
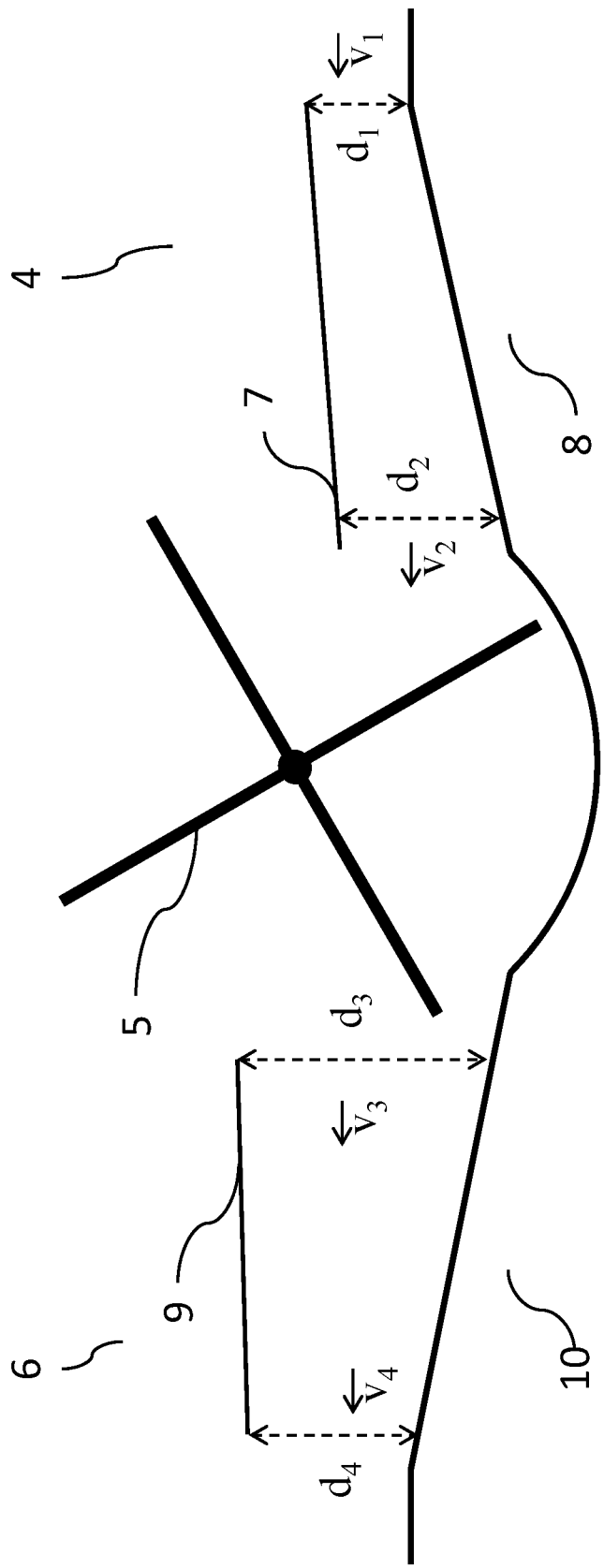
FIG. 2 is a cross-sectional view taken along lines A-A of FIG. 1.

FIG. 2 is a cross-sectional view taken along lines A-A of the system of FIG. 1 illustrating a level bottom, variable depth contraction zone 4, and a variable depth expansion zone 6. The surface 7 of the algae cultivation fluid entering the pumping, and the surface 9 of the fluid exiting the pump 5 is open to the air. A bottom 8 of the channel 100 in the contraction zone 4, and a bottom 10 of the channel 100 in the expansion zone 6 are sloped downwardly toward the pump 5 to maintain a substantially constant cross-sectional area. The pump 5 is illustrated as a paddlewheel, but the pump can be any device or structure suitable for increasing the algae cultivation fluid elevation from the surface 7 of the fluid entering the pump 5 to the surface 9 of the fluid exiting the pump 5. When the algae cultivation fluid is circulating in the channel 100, the depth d3 of fluid exiting the pump 5 is the greatest, while the depth of the fluid going away from the exit of the pump 5 decreases to d4 so as to maintain a constant cross-sectional area of the algae cultivation fluid throughout the expansion zone 6. In an embodiment, the cross-sectional area of the algae cultivation fluid in the channel 100 can be defined as the depth of the algae fluid depth times a width of the channel 100. The elevation of the surface 9 of the algae cultivation fluid decreases in the expansion zone 6 to overcome energy loss in the zone 6. The algae cultivation fluid depth decreases from depth d4 to depth d1 to overcome energy loss in the channels 1 and 2 and bends 3a and 3b. The algae cultivation fluid depth increases to d2 in the contraction zone 4 as the fluid leads into the entry of the pump 5 so as to maintain a substantially constant cross-sectional area in the contraction zone 4. The elevation of the surface 7 of the algae cultivation fluid in the contraction zone 4 decreases to overcome the energy loss in the zone 4. It should therefore be appreciated that in the system of FIGS. 1 and 2, the depth of the contraction zone 4 is greater than a depth of at least a portion the channel 100 outside the contraction zone 4, and the depth of the expansion zone 6 is greater than a depth of at least a portion of the channel 100 outside the expansion zone. It should likewise be appreciated that in the system of FIGS. 1 and 2, the depth of the contraction zone 4 increases leading into the entrance of the pump 5, and the depth of the expansion zone 6 decreases going away from the exit of the pump 5.

Because the cross-sectional area of the algae cultivation fluid is constant in the contraction zone 4, the algae cultivation fluid velocity is constant in the contraction zone 5, and V1 entering the contraction zone 4 is equal or substantially equal to V2. The velocity V3 of the algae cultivation fluid exiting the pump 5 is lower than the velocity V2 entering the pump. The velocity V4 exiting the expansion zone 6 is the same or substantially the same as the velocity V3 entering the expansion zone 6 because the cross-sectional area in the expansion zone 6 is constant or substantially constant. The energy loss for flow in the contraction 4 and expansion 6 zones is low because the velocity is constant in each of the zones. Furthermore, the lower velocity in the contraction 4 and expansion 6 zones relative to a contraction zone or expansion zone without increasing depth as the width decrease results in lower energy losses in the systems. The constant or substantially constant cross-sectional area resulting from the increased depth in the contraction and expansion zones can be used with sloped or level open raceway algae cultivation systems.

Figure 3:
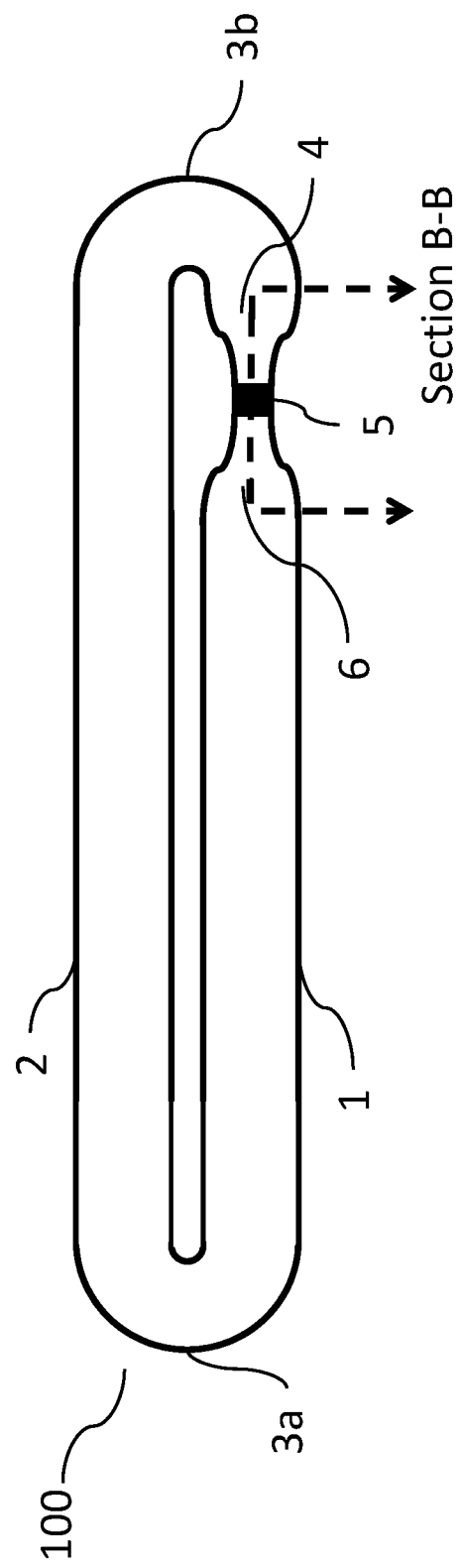
FIG. 3 is a plan view illustrating an open raceway algae cultivation system according to another embodiment of the present disclosure.
Figure 4:
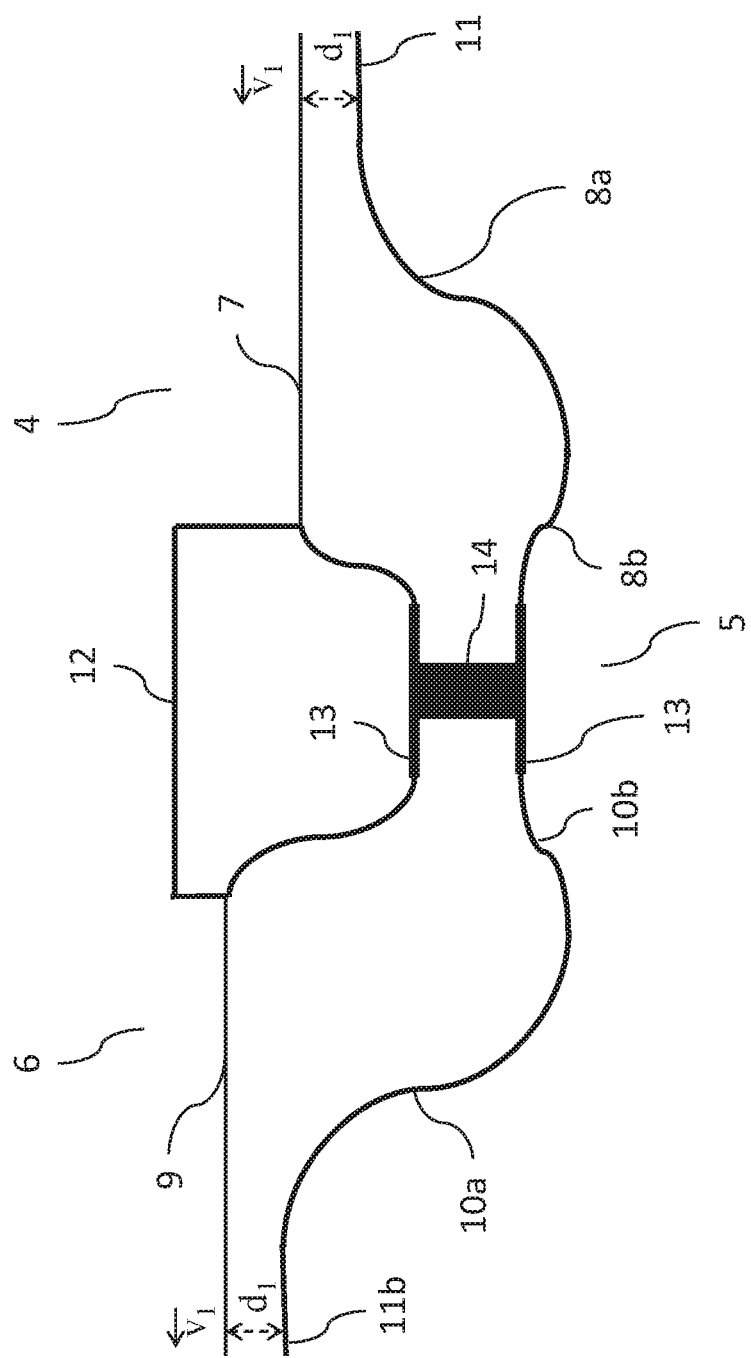
FIG. 4 is a cross-sectional view taken along lines B-B of FIG. 3.

FIGS. 3 and 4 illustrate another non-limiting embodiment of an open raceway algae cultivation system of the present disclosure. The system of FIGS. 3 and 4 is similar to the system illustrated in FIGS. 1 and 2, except that the rate of change in the width and depth of the contraction 4 and expansion 6 zones are non-linear. The system of FIGS. 3 and 4, like the system of FIG. 1, includes a channel 100 having two conduits 1 and 2 that are fluidly coupled or connected to each other by bends 3a, 3b. The algae cultivation fluid in the channel 100 is circulated by pump 5, which again can be a paddlewheel, propeller pump, an Archimedes screw pump, a fluid jet, or any other suitable device or structure for pumping the algae cultivation fluid in the channel 100. The width of the pump 5 is less than the width of the channels 1 and 2 so that leading into an entrance of the pump 5 there is a contraction zone 4 having a width that is less than a width of the channel 100 outside of the contraction zone 4. The width of contraction zone 4 decreases from the portion outside the contraction zone 4 leading into the entrance of the pump 5. The width of pump 5 is also less than the conduits 1 and 2 so that going away from the exit of the pump 5, there is an expansion zone 6 having a width greater than the width of channel 100 outside the expansion zone 6. The width of expansion zone 6 increases going away from the exit of pump 5. When algae cultivation fluid is circulated in the channel 100 via pump 5, the fluid exits the pump 5, flows through the expansion zone 6, through the conduit 1, around bend 3a, through conduit 2, around bend 3b, through contraction zone 4, and back into the entrance of pump 5. The bottom of the conduits 1 and 2, as well as the bends 3a and 3b, can be level or sloped downwardly from the expansion zone 6 to the contraction zone 4.

Referring more specifically to FIG. 4, FIG. 4 is a cross-sectional view of the system of FIG. 3 taken along lines B-B. FIG. 4 shows sloped bottoms 11, 12, along with variable depth contraction 4 and expansion 6 zones. The surface 7 of the algae cultivation fluid entering the pump 5, and the surface 9 of the algae cultivation fluid exiting the pump 5 is open to the air. The bottom 8 of the channel 100 in the contraction zone 4, and the bottom 10 of the channel 100 in the expansion zone 6 are varied to minimize the energy losses or velocity gradients in the zones. The pump 5 is illustrated as a propeller pump 14 located in a pipe 13 of a barrier 12, between the contraction zone 4 and the expansion zone 6. It should be appreciated again, however, that pump 5 can be any suitable device or structure for increasing the algae cultivation fluid elevation from the surface 7 entering the pump 5 to the surface 9 exiting the pump 5.

The bottoms 11 and 12 of the channel 100 are sloped downwardly to overcome energy loss in the conduits 1 and 2 and bends 3a and 3b, while maintaining a substantially constant depth d1. The cross-sectional area through channel 1, bend 3a, channel 2, and bend 3b is constant or substantially constant because the width and depth are substantially constant. The cross-sectional area in the contraction zone 4 is constant or substantially constant for a portion of the contraction zone as the depth 8a increases, while the width of the channel decreases. The cross-sectional area of pipe 13, defined as $\pi r^2$, where r is the radius of pipe, is smaller than the cross-sectional area of the channel d1 times the width of the channel. The cross-sectional rea of fluid must vary entering the pump 5 to accommodate the lower cross sectional area of the pump 5. The depth 8b of the contraction zone 4 and cross-sectional area of the fluid is varied entering the pump 5 such that the energy loss is minimized. Similarly, the depth 10b of the expansion zone 6 is varied exiting the pump 5 such that the energy loss is minimized. The depth of the expansion zone 10a is varied to match the increase in width such that the cross-sectional area is constant or substantially constant. The shape of the barrier 12 is also varied to further minimize the energy loss in decreasing the cross-sectional area to enter and exit the pipe 13. The velocity of the circulating algae cultivation fluid is inversely proportional to the cross-sectional area, so the velocity V1 is constant in most of the expansion zone 6, circulating in the channels 1 and 2 and bends 3a and 3b, and most of the contraction zone 4. The energy loss for flow in the contraction 4 and expansion 6 zones is therefore low because the velocity is constant or substantially constant in a large portion of the zones and the shape of the bottom entering the pump 5 is varied to minimize the energy loss. This approach illustrated in FIG. 4 can be used with a sloped or level open raceway algae cultivation system. It should therefore be appreciated that in the system of FIGS. 3 and 4, the depth of the contraction zone 4 is greater than a depth of at least a portion the channel 100 outside the contraction zone 4, and the depth of the expansion zone 6 is greater than a depth of at least a portion of the channel 100 outside the expansion zone.

What is claimed is:

1. An open raceway algae cultivation system comprising:
    a channel configured to contain an algae cultivation fluid, the channel including a contraction zone having a width and a depth and an expansion zone having a width and a depth; and
    a pump configured to circulate the algae cultivation fluid in the channel, the pump including an entrance and an exit,
    wherein (i) the width of the contraction zone decreases leading into the entrance of the pump, and (ii) the depth of the contraction zone is greater than a depth of at least a portion of the channel located outside of the contraction zone,
    wherein the depth of the contraction zone varies such that, when the algae cultivation fluid is circulated in the channel, a cross-sectional area of the algae cultivation fluid in the contraction zone is substantially the same as an average cross-sectional area of the algae cultivation fluid outside of the contraction zone, and
    wherein a bottom of the channel at a beginning of the contraction zone is lower than a bottom of the channel at an outlet of the expansion zone.

2. The open raceway algae cultivation system of claim 1, wherein (i) the width of the expansion zone increases going away from the exit of the pump, and (ii) wherein the depth of the expansion zone is greater than a depth of at least a portion of the channel located outside the expansion zone.

3. The open raceway algae cultivation system of claim 1, wherein the depth of the contraction zone varies such that, when the algae cultivation fluid is circulated in the channel, energy loss is minimized as the algae cultivation fluid circulates from outside the contraction zone, through the contraction zone, to the pump.

4. The open raceway algae cultivation system of claim 1, wherein the pump includes one of (i) a paddlewheel, (ii) a propeller pump, or (iii) an Archimedes screw pump.

5. The open raceway algae cultivation system of claim 1, wherein the depth of the contraction zone varies such that, when the algae cultivation fluid is circulated in the channel, the depth of the algae cultivation fluid in the contraction zone varies such that velocity gradients for the algae cultivation fluid are minimized as the fluid circulates from outside the contraction zone, through the contraction zone, to the pump.

6. The open raceway algae cultivation system of claim 1, wherein the depth of the contraction zone increases leading into the entrance of the pump.

7. The open raceway algae cultivation system of claim 1, wherein the depth of the expansion zone decreases going away from the exit of the pump.

8. The open raceway algae cultivation system of claim 7, a rate of change of at least one of the width or depth in the expansion zone is linear.

9. The open raceway algae cultivation system of claim 7, wherein a rate of change of at least one of the width or depth in the expansion zone is non-linear.

10. The open raceway algae cultivation system of claim 1, wherein a cross-sectional area of the algae cultivation fluid at a cross-section in the channel is defined by a depth of the algae fluid times a width of the channel at that cross-section.

11. The open raceway algae cultivation system of claim 1, wherein a lower end of the contraction zone continuously decreases from a portion outside the contraction zone leading into the entrance of the pump.

12. An open raceway algae cultivation system comprising:
    a channel configured to contain an algae cultivation fluid, the channel including an expansion zone having a width and a depth and a contraction zone having a width and a depth; and
    a pump configured to circulate the algae cultivation fluid in the channel, the pump including an entrance and an exit,
    wherein (i) the width of the expansion zone increases going away from the exit of the pump, and (ii) the depth of the expansion zone is greater than a depth of at least a portion of the channel located outside of the expansion zone, and
    wherein the depth of the expansion zone varies such that, when the algae cultivation fluid is circulated in the channel, a depth of the algae cultivation fluid in the expansion zone varies so that a cross-sectional area of the algae cultivation fluid in the expansion zone is substantially the same as an average cross-sectional area of the algae cultivation fluid outside of the expansion zone, and
    wherein a bottom of the channel at a beginning of the contraction zone is lower than a bottom of the channel at an outlet of the expansion zone.

13. The open raceway algae cultivation system of claim 12, wherein the depth of the expansion zone varies such that when the algae cultivation fluid is circulated in the channel, the depth of the algae cultivation fluid in the expansion zone varies to minimize energy loss as the algae cultivation fluid circulates from the pump, through the expansion zone, to outside the expansion zone.

14. The open raceway algae cultivation system of claim 12, wherein the depth of the expansion zone varies such that, when the algae cultivation fluid is circulated in the channel, the depth of the algae cultivation fluid in the expansion zone varies so that velocity gradients are minimized as the algae cultivation fluid flows from the pump, through the expansion zone, to outside the expansion zone.

15. The open raceway algae cultivation system of claim 12, wherein the pump includes one of (i) a paddlewheel, (ii) a propeller pump, or (iii) an Archimedes screw pump.

16. The open raceway algae cultivation system of claim 12, wherein a cross-sectional area of the algae cultivation fluid at a cross-section in the channel is a depth of the algae fluid times a width of the channel at that cross-section.

* * * * *